United States Patent [19]

Okamura et al.

[11] Patent Number: 4,751,173
[45] Date of Patent: Jun. 14, 1988

[54] PROCESS FOR HARDENING GELATIN

[75] Inventors: Hisashi Okamura; Hiroshi Kawamoto, both of Kanagawa, Japan

[73] Assignee: Fuji Photo Film Co., Ltd., Kanagawa, Japan

[21] Appl. No.: 946,729

[22] Filed: Dec. 29, 1986

[30] Foreign Application Priority Data

Dec. 27, 1985 [JP] Japan .................. 60-293927
Feb. 26, 1986 [JP] Japan .................. 61-41296

[51] Int. Cl.$^4$ .......................... G03C 5/36; G03C 1/30
[52] U.S. Cl. .................................... 430/451; 430/621; 430/623; 430/426; 530/354
[58] Field of Search ............... 430/621, 623, 626, 420, 430/426, 451; 530/354

[56] References Cited

U.S. PATENT DOCUMENTS 4,067,741 1/1978 Bergthaller et al. ............. 430/621
4,123,281 10/1978 Monbaliu et al. ................. 430/623
4,233,398 11/1980 Nittel et al. ........................ 430/621
4,421,847 12/1983 Jung et al. ......................... 430/621

FOREIGN PATENT DOCUMENTS 84850 1/1976 Japan .

Primary Examiner—Paul R. Michl
Assistant Examiner—Mark R. Buscher
Attorney, Agent, or Firm—Sughrue, Mion, Zinn, Macpeak & Seas

[57] ABSTRACT

A process for hardening gelatin, which comprises incorporating in a gelatin-containing material at least one hardening compound represented by formula (I)

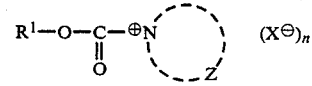

wherein $R^1$ represents a substituted or unsubstituted aryl group, Z represents non-metallic atoms necessary for the formation of a nitrogen-containing heteroaromatic ring which may optionally be substituted, $X^\ominus$ represents an anion, and n represents 0 or 1 provided that when n represents 0, the compound forms an inner salt. The gelatin hardeners can rapidly harden gelatin with little or no post-hardening and react with reactive groups of gelatin with high selectivity.

24 Claims, No Drawings

PROCESS FOR HARDENING GELATIN

FIELD OF THE INVENTION

This invention relates to a process for hardening gelatin using an improved hardener, and more particularly to a process for hardening gelatin used for silver halide photographic light-sensitive materials.

BACKGROUND OF THE INVENTION

Gelatin is commonly used in a layered form as a binder in many photographic light-sensitive materials. It has so far been known to harden gelatin using various compounds for the purposes of enhancing water resistance and mechanical strength of the gelatin layer.

For example, known hardeners include aldehyde compounds such as formaldehyde and glutaraldehyde, compounds having a reactive halogen or halogens as described in U.S. Pat. No. 3,288,775, etc., compounds having a reactive, ethylenically unsaturated bond or bonds as described in U.S. Pat. No. 3,642,486, Japanese Patent Publication No. 13563/74, etc., aziridine compounds as described in U.S. Pat. No. 3,017,280, etc., epoxy compounds as described in U.S. Pat. No. 3,091,537, etc., halogen-carboxylaldehydes such as mucochloric acid, etc., dioxanes such as dihydroxydioxane, dichlorodioxane, etc., and inorganic hardeners such as chromium alum, zirconium sulfate, etc.

However, when used in photographic light-sensitive materials, all of these known gelatin hardeners have some drawbacks, such as that only an insufficient hardening effect is provided, that the hardening degree varies with a long period of time, called "post-hardening", due to a slow hardening reaction with gelatin, that detrimental influences (particularly, an increase of fog, a reduction of sensitivity, etc.) are exerted on the properties of photographic light-sensitive materials, that the hardening effect is lost due to other coexisting photographic additives, or that effects of other photographic additives (for example, couplers for color light-sensitive materials) are deteriorated.

As hardeners which exhibit a comparatively rapid hardening reaction with gelatin, and therefore, cause less post-hardening, there are known compounds having a dihydroquinoline skeleton, described in U.S. Pat. No. 4,013,468; compounds having a phosphorus-halogen bond, described in Japanese Patent Application (OPI) No. 113929/83 (the term "OPI" as used herein refers to a "published unexamined Japanese patent application"); compounds having an N-sulfonyloximido group, described in U.S. Pat. No. 4,111,962; compounds having two or more N-acyloxyimino groups within them, described in Japanese Patent Publication No. 22089/78; N-carbamoylpyridinium salts described in U.S. Pat. Nos. 3,880,665 and 4,063,952; and 2-sulfonyloxypyridinium salts described in Japanese Patent Application (OPI) No. 110762/81.

These hardeners have the characteristic properties that they cause less post-hardening due to their fast hardening action. However, although they cause a fast hardening reaction with gelatin, at the same time they are subject to the side reaction of being decomposed with water. Therefore, in the common process of preparing a light-sensitive material using a gelatin aqueous solution, the efficiency of the hardener is so low that, in order to obtain a gelatin layer with a desired hardening degree, a large amount of hardener must be used.

Hardeners as described in U.S. Pat. Nos. 3,880,665 and 4,063,952, Japanese Patent Application (OPI) No. 110762/81, etc., are generally believed to undergo a nucleophilic attack with carboxyl or amino groups of gelatin to react therewith, thus hardening gelatin. In preparing a gelatin layer, an aqueous gelatin solution is usually used. Since coexisting water has some nucleophilic properties, it unavoidably tends to react with the hardener to decompose and render the hardener powerless. This tendency is serious with those hardeners which show a fast hardening action. Therefore, in order to harden gelatin rapidly with good efficiency, development of hardeners which react with carboxyl groups, amino groups or the like of gelatin faster than with water, i.e., which well selectively react with gelatin, is of great importance. Hardeners such as N-carbamoylpyridinium salts and 2-sulfonyloxypyridinium salts have the defect that they have such a poor efficiency, which may be attributed to low selectivity as described above, that hardeners which have a higher efficiency, which harden gelatin rapidly, and which have a high water solubility have been eagerly desired to be developed.

SUMMARY OF THE INVENTION

An object of the present invention is to provide a process for hardening gelatin by using a novel gelatin hardener.

Another object of the present invention is to provide gelatin hardeners which can rapidly harden gelatin, and which cause less post-hardening.

A further object of the present invention is to provide gelatin hardeners which react with reactive groups of gelatin with high selectivity, to thereby effectively harden gelatin.

These and other objects of the present invention will become apparent from the following description thereof.

As a result of intensive investigations, the inventors have found that the above-described and other objects of the present invention can be attained by incorporating in a gelatin-containing material as gelatin hardeners at least one compound represented by formula (I)

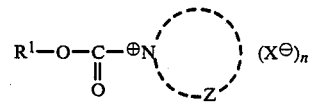

wherein $R^1$ represents a substituted or unsubstituted aryl group, Z represents non-metallic atoms necessary for the formation of a nitrogen-containing heteroaromatic ring which may optionally be substituted, $X^\ominus$ represents an anion, and n represents 0 or 1 provided that when n represents 0, the compound forms an inner salt.

DETAILED DESCRIPTION OF THE INVENTION

In more detail, $R^1$ represents an aryl group having from 6 to 20 carbon atoms (e.g., a phenyl group, a naphthyl group, etc.). $R^1$ preferably has a substituent or substituents. The number of the substituents may be one to five. When $R^1$ has two or more substituents, they may be the same or different. Examples of the substituents include a halogen atom,

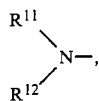

a straight or branched chain alkyl group having from 1 to 20 carbon atoms (e.g., a methyl group, an ethyl group, an isopropyl group, an isobutyl group, a tert-butyl group, etc.), an alkoxy group having from 1 to 20 carbon atoms (e.g., a methoxy group, an ethoxy group, an isopropyloxy group, etc.), an aryl group having from 6 to 20 carbon atoms (e.g., a phenyl group, a naphthyl group, etc.), an aryloxy group having from 6 to 20 carbon atoms (e.g., a phenoxy group, a naphthoxy group, etc.), an aralkyl group having from 7 to 20 carbon atoms (e.g., a benzyl group, a phenethyl group, etc.), an alkenyl group having from 2 to 20 carbon atoms (e.g., a vinyl group, a propenyl group, etc.), a sulfo group, a sulfoalkyl group, etc.

$R^{11}$ and $R^{12}$ each represents the same substituents as defined for $R^1$ (except for a halogen atom and

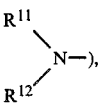

or $R^{11}$ and $R^{12}$ may be taken together to form a ring.

Z represents non-metallic atoms necessary for the formation of a nitrogen-containing heteroaromatic ring which may optionally be substituted, and preferably, non-metallic atoms necessary for the formation of a nitrogen-containing 5- or 6-membered heteroaromatic ring which may optionally be substituted.

Preferable examples of the heteroaromatic ring formed by Z and one nitrogen atom include a pyridine ring, a pyrimidine ring, a pyrazole ring, an imidazole ring, a triazole ring, a tetrazole ring, an oxazole ring, a thiazole ring, etc. and benzo-condensed rings thereof, with a pyridine ring and an imidazole ring being particularly preferable. The formed heteroaromatic ring may be substituted.

The ring may have 1 to 5 substituents and, when they have two or more substituents, the substituents may be the same or different. Examples of substituents include a halogen atom,

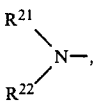

a straight or branched chain alkyl group having from 1 to 20 carbon atoms, an alkoxy group having from 1 to 20 carbon atoms, an aryl group having from 6 to 20 carbon atoms, an aryloxy group having from 6 to 20 carbon atoms, an aralkyl group having from 7 to 20 carbon atoms, an alkenyl group having from 2 to 20 carbon atoms, a sulfo group, a sulfoalkyl group, etc.

Where the substituent is a sulfo group or a sulfoalkyl group, $X^\ominus$ and Z are preferably bound to each other to form an inner salt.

$R^{21}$ and $R^{22}$ are the same as defined for the substituents of $R^1$ (except for a halogen atom and

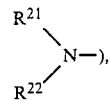

or $R^{21}$ and $R^{22}$ may be bound to each other to form a ring.

$X^\ominus$ represents an anion exemplified by a halide ion, an alkylsulfonate ion (having from 1 to 20 carbon atoms), an arylsulfonate ion (having from 6 to 20 carbon atoms), a sulfate ion, a phosphonate ion, a phosphate ion, $BF_4^\ominus$, $ClO_4^\ominus$, $PF_6^\ominus$, etc. Particularly preferable examples thereof are $Cl^\ominus$, $BF_4^\ominus$, $PF_6^\ominus$, an alkylsulfonate ion, and an arylsulfonate ion.

When n represents 0, $X^\ominus$ and the nitrogen-containing heteroaromatic ring are bonded to each other to form an inner salt.

Examples of the compounds to be used in the present invention are described below which, however, do not limit the present invention in any way.

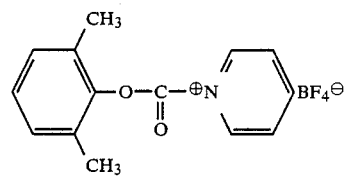

Compound 1

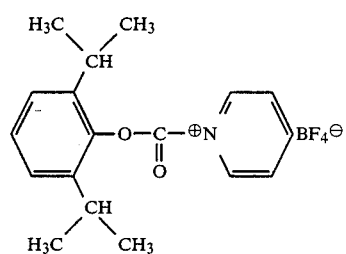

Compound 2

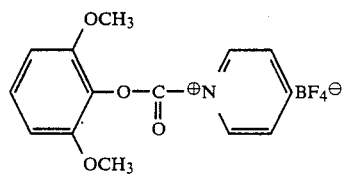

Compound 3

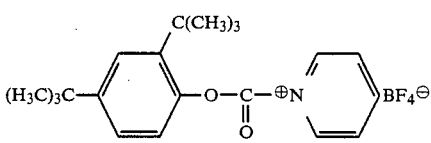

Compound 4

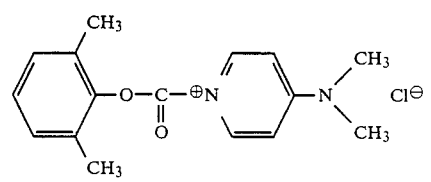

Compound 5

-continued
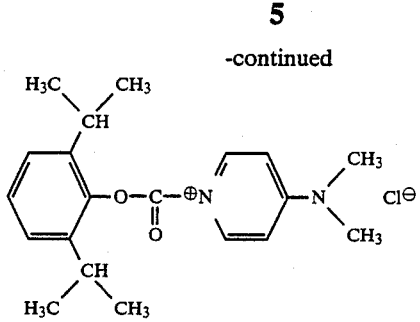
Compound 6
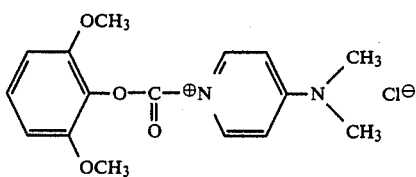
Compound 7
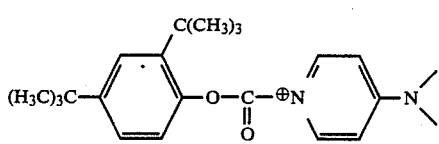
Compound 8
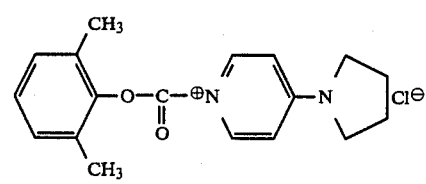
Compound 9
Compound 10
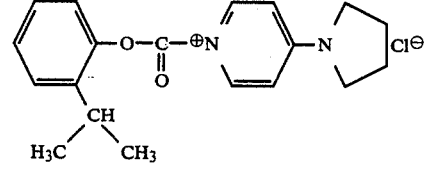
Compound 11
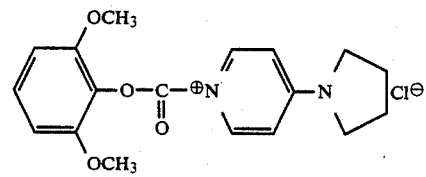
Compound 12
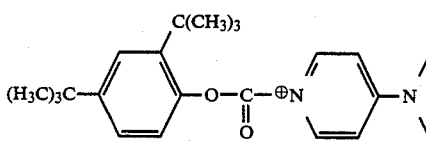
Compound 13
-continued
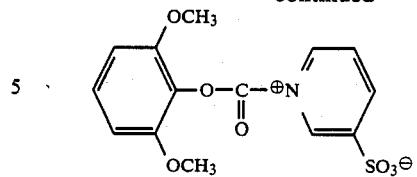
Compound 14
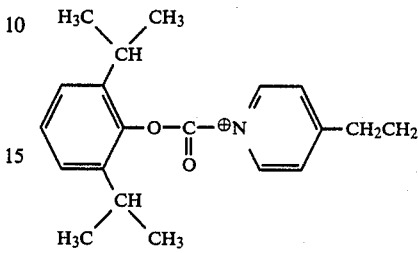
Compound 15
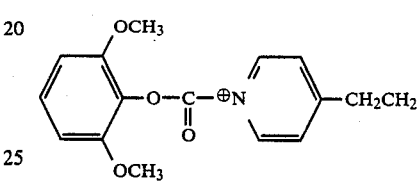
Compound 16
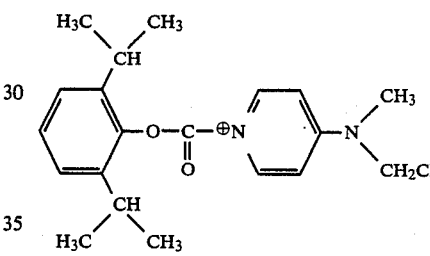
Compound 17
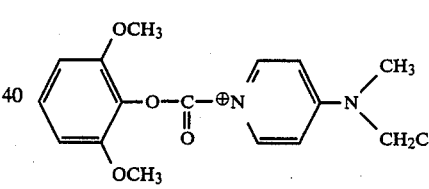
Compound 18
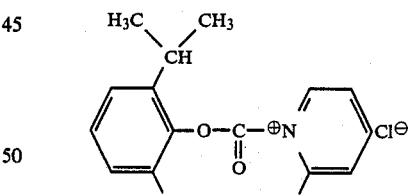
Compound 19
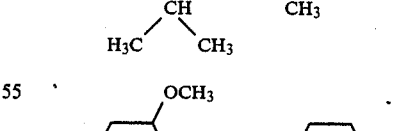
Compound 20
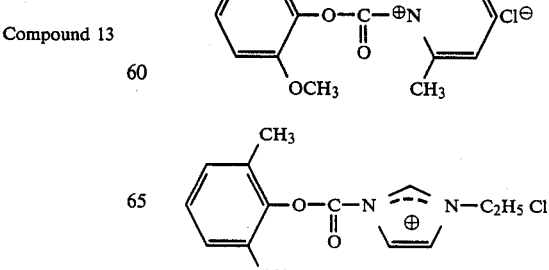
Compound 21

-continued
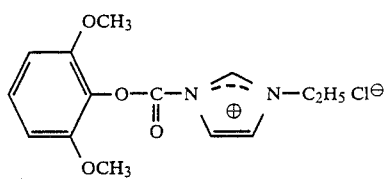
Compound 22
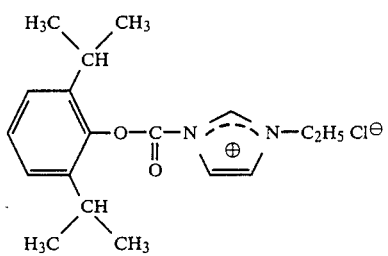
Compound 23
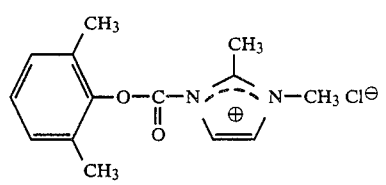
Compound 24
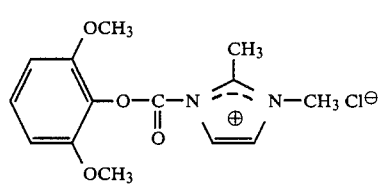
Compound 25
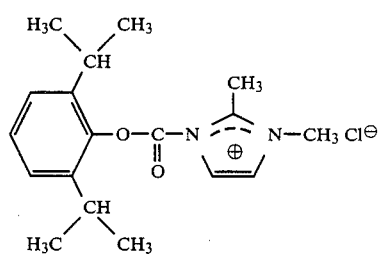
Compound 26
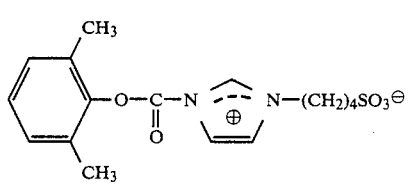
Compound 27
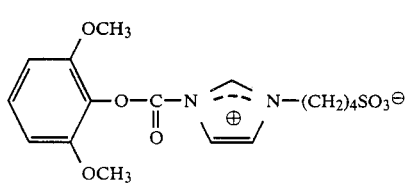
Compound 28
-continued
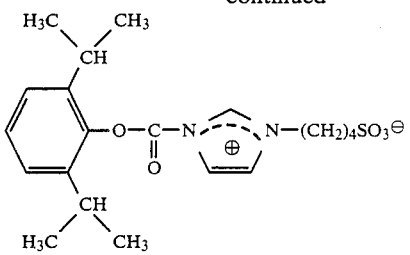
Compound 29
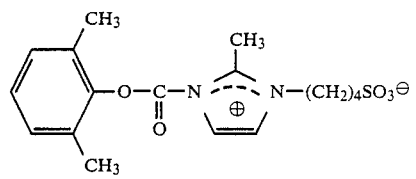
Compound 30
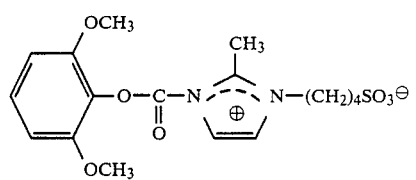
Compound 31
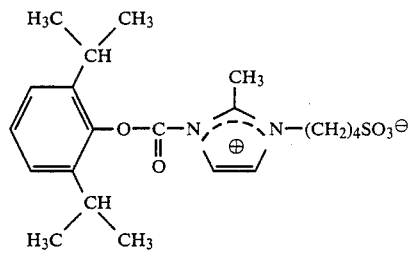
Compound 32
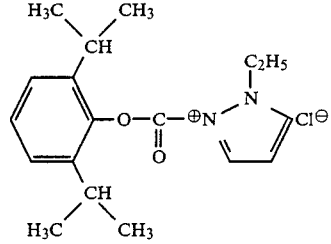
Compound 33
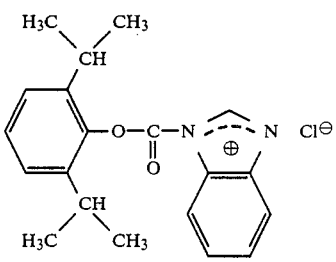
Compound 34
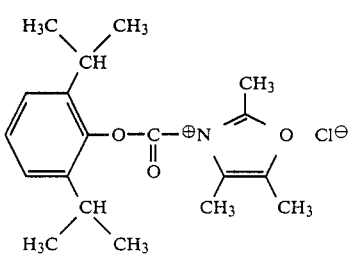
Compound 35

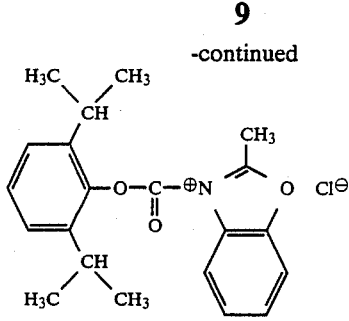

Compound 36

Synthesis examples of these compounds of the present invention are described below.

SYNTHESIS EXAMPLE 1

(Synthesis of Compound 2)

A solution of 4.3 g of 2,6-diisopropylphenyl chlorocarbonate in 15 ml of THF (tetrahydrofuran) was dropwise added to a solution of 1.7 g of pyridine in 15 ml of THF under cooling with ice-water. After completion of the dropwise addition, the mixture was stirred for one hour at room temperature, then 50 ml of 1,2-dichloroethane and 4.2 g of $NH_4BF_4$ were added thereto, followed by stirring for 30 minutes at room temperature. After filtering off insolubles, the filtrate was concentrated under reduced pressure. Then, 100 ml of ether was added thereto, and crystals precipitated were collected by filtration and dried to obtain Compound 2 (yield: 4.5 g).

The chemical structure of the compound was identified by an NMR spectrum, an IR spectrum, and an elemental analysis.

SYNTHESIS EXAMPLE 2

(Synthesis of Compound 5)

A solution of 3 g of 2,6-dimethylphenyl chlorocarbonate in 20 ml of THF was dropwise added to a solution of 2 g of 4-(N,N-dimethylamino)pyridine in 50 ml of THF under cooling with ice-water. After completion of the dropwise addition, the mixture was stirred for 2 hours at room temperature. White crystals precipitated were collected by filtration, washed with a small amount of THF, then dried to obtain compound 5 (yield: 4.7 g).

The chemical structure of the compound was identified by an NMR spectrum, an IR spectrum, and an elemental analysis.

SYNTHESIS EXAMPLE 3

(Synthesis of Compound 10)

A solution of 2.4 g of 2,6-diisopropylphenyl chlorocarbonate in 10 ml of THF was dropwise added to a solution of 1.5 g of 4-pyrrolidinopyridine in 80 ml of THF under cooling with ice-water. After completion of the dropwise addition, the mixture was stirred for 2 hours at room temperature. White crystals precipitated were collected by filtration, washed with a small amount of THF, then dried to obtain Compound 10 (yield: 3.5 g).

The chemical structure of the compound was identified by an NMR spectrum, an IR spectrum, and an elemental analysis.

SYNTHESIS EXAMPLE 4

(Synthesis of Compound 23)

A solution of 6 g of 2,6-diisopropylphenyl chlorocarbonate in 10 ml of THF was dropwise added to a solution of 2.4 g of N-ethylimidazole in 100 ml of THF. After completion of the dropwise addition, the mixture was stirred as such for 2 hours. White crystals precipitated were collected by filtration, washed with a small amount of THF, then dried to obtain Compound 23 (yield: 6.7 g).

The chemical structure of the compound was identified by an NMR spectrum, an IR spectrum, and an elemental analysis.

Compounds other than the compounds described in above Synthesis Examples may also be synthesized according to these processes or analogous processes thereof.

When these compounds are applied to gelatin-containing photographic layers as hardeners, unfavorable phenomena such as fogging, deterioration of photographic properties (e.g., densensitization), formation of stains, reaction with couplers contained in color photographic light-sensitive materials, etc., are scarcely observed. In addition, hardening proceeds so rapidly that the hardening degree reaches its final level within a few days after coating, after which the hardening degree does not increase, i.e., substantially no post-hardening is observed.

The amount of the hardeners of the present invention to be used may be freely selected according to the particular end-use intended. Usually, the hardener can be used in an amount of from 0.01 to 20 wt% based on the weight of dry gelatin (i.e., dry to the touch), particularly preferably from 0.05 to 10 wt%.

The hardeners of the present invention may also be effectively used for partly hardening gelatin in the process of elongating the chain of gelatin by partial hardening as described in Japanese Patent Application (OPI) No. 2324/81. Further, the hardeners can be used for hardening the thus elongated gelatin.

The hardeners of the present invention can be used for all photographic light-sensitive materials using gelatin. For example, they can be used for color negative films, color reversal films, color positive films, color photographic printing papers, color reversal photographic printing papers, color light-sensitive materials of a color diffusion transfer process or a silver-dye bleach process, and black-and-white light-sensitive materials such as a black-and-white films, X-ray films, films for a photomechanical process, black-and-white photographic printing papers, aerial photographic films, microfilms, facsimilies, photocomposing films or printing papers, and graphic films.

In applying to these materials, photographic layers to which the hardener of the present invention is added are not particularly limited, and may be added to any gelatin-containing photographic layer including light-insensitive layers such as a subbing layer, a backing layer, a filter layer, an interlayer, an overcoating layer, etc., as well as to silver halide emulsion layers.

The hardeners of the present invention may be used alone or in a combination of two or more. Further, they may be used in combination with other conventionally known hardeners.

As known hardeners, there are illustrated aldehydes such as formaldehyde and glutaraldehyde, ketone compounds such as diacetyl and cyclopentanedione, compounds having a reactive halogen such as bis(2-chloroethylurea), 2-hydroxy-4,6-dichloro-1,3,5-triazine, and those compounds which are described in U.S. Pat. Nos. 3,288,775 and 2,732,303, British Pat. Nos. 974,723 and 1,167,207, etc., compounds having a reactive olefin such as divinylsulfone, 5-acetyl-1,3-diacryloylhexahydro-1,3,5-triazine, and those compounds which are described in U.S. Pat. Nos. 3,635,718 and 3,232,763, British Pat. No. 994,869, etc., N-methylol compounds such as N-hydroxymethylphthalimide and those which are described in U.S. Pat. Nos. 2,732,316 and 2,586,168, etc., isocyanates described in U.S. Pat. No. 3,103,437, aziridine compounds described in U.S. Pat. Nos. 3,017,280, 2,983,611, etc., acid derivatives described in U.S. Pat. Nos. 2,725,294, 2,725,295, etc., carbodiimide compounds described in U.S. Pat. No. 3,100,704, etc., epoxy compounds described in U.S. Pat. No. 3,091,537, etc., isoxazole compounds described in U.S. Pat. Nos. 3,321,313 and 3,543,292, halogencarboxyaldehydes such as mucochloric acid, dioxane derivatives such as dihydroxydioxane and dichlorodioxane, the aforementioned dihydroquinoline compounds, compounds having a phosphorus-halogen bond, N-sulfonyloxyimide compounds, N-acyloxyimino compounds, N-carbonyloxyimide compounds described in Japanese Patent Application (OPI) No. 43353/81, 2-sulfonyloxypyridinium salts, N-carbamoylpyridinium salts, and the like. As inorganic hardeners, there are illustrated chromium alum, zirconium sulfate, etc. In addition, the compounds of the present invention may be used together with the precursors of the above-described compounds, such as alkali metal bisulfitealdehyde adducts, methylol derivatives of hydantion, primary aliphatic nitroalcohols, mesyloxyethylsulfonyl compounds, chloroethylsulfonyl compounds, etc. in place of the above-described compounds. In the case of using the hardeners of the present invention in combination with other hardeners, the proportion of the hardeners of the present invention may be freely selected depending upon the end-use and effect. However, the hardeners of the present invention are preferably used in a proportion of 50 mol% or more.

The hardeners of the present invention can be used in combination with those compounds which accelerate hardening of gelatin. For example, the polymers described in Japanese Patent Application (OPI) No. 4141/81 and having sulfinic acid groups may be used in the system of the hardener of the present invention and a vinylsulfone type hardener as hardening accelerators.

Gelatin to which the hardener of the present invention is applied may be any of so-called alkali-processed (or lime-processed) gelatin which has been dipped in an alkali bath in the gelatin production process before being extracted; acid-processed gelatin having been dipped in an acid bath; double-dipped gelatin having been subjected to both processings; and enzyme-processed gelatin as described in *Bull. Soc. Sci. Photo. Japan*, No. 16, p. 30 (1966). Further, the hardener of the present invention can be applied to a low-molecular weight gelatin prepared through partial hydrolysis of these gelatins by heating in a water bath or by having protease act thereon.

Gelatins to which the hardeners of the present invention are applied may, if desired, be partly replaced by colloidal albumin, casein, cellulose derivatives (e.g., carboxymethyl, cellulose, hydroxyethylcellulose, etc.), sugar derivatives (e.g., agar-agar, sodium alginate, starch derivatives, dextran, etc.), synthetic hydrophilic colloids (e.g., polyvinyl alcohol, poly-N-vinylpyrrolidone, polyacrylic acid copolymer, polyacrylamide or derivatives or partially hydrolyzed products thereof, etc.), or by so-called gelatin derivatives prepared by treating gelatin with a reagent having one group capable of reacting with a functional group contained in the gelatin, i.e., an amino group, an imino group, a hydroxy group, or a carboxy group to thereby modify the gelatin, or graft polymers prepared by grafting a molecular chain of other high molecular substances.

In the case of using the hardener of the present invention in photographic light-sensitive materials, the photographic emulsion layers and other layers thereof may contain synthetic polymers such as a latex-type vinyl compound polymer dispersed in water, particularly a compound capable of increasing dimensional stability of the photographic materials, alone or as a mixture, or in combination with a hydrophilic water-permeable colloid.

In the case of using the hardener of the present invention in photographic light-sensitive materials, a matting agent may be used together with it. As the matting agent, water-insoluble organic or inorganic fine particles of 0.2 $\mu$m to 10 $\mu$m, particularly 0.3 $\mu$m to 5 $\mu$m, in average particle size can be used.

The gelatin hardeners of the present invention may be used together with various color couplers.

Specific examples of the cyan, magenta, and yellow couplers which may be used in the present invention are described in the patents cited in *Research Disclosure*, RD No. 17643 (December 1978), item VII-D and ibid., RD No. 18717 (November 1979).

The color couplers to be incorporated in light-sensitive materials are preferably made diffusion-resistant by introducing a ballast group or by polymerization. Two-equivalent color couplers wherein coupling-active sites are substituted by coupling-off groups can reduce the amount of coated silver in comparison with 4-equivalent color couplers wherein coupling-active sites are occupied by hydrogen atom, thus providing higher sensitivity. Couplers which produce a colored dye having a proper diffusability, colorless couplers, DIR couplers capable of releasing a development inhibitor upon a coupling reaction, or couplers capable of releasing a development accelerator may also be used.

Typical examples of yellow couplers which may be used together with the gelatin hardeners of the present invention include oil protect type acylacetamide couplers. Specific examples of such a yellow coupler include those described in U.S. Pat. Nos. 2,407,210, 2,875,057 and 3,265,506. In the present invention, a diequivalent yellow coupler may be preferably used. Typical examples of such a diequivalent yellow coupler include oxygen atom releasing yellow couplers as described in U.S. Pat. Nos. 3,408,194, 3,447,928, 3,933,501 and 4,022,620, and nitrogen atom releasing yellow couplers as described in Japanese Patent Publication No. 10739/83, U.S. Pat. Nos. 4,401,752 and 4,326,024, *Research Disclosure*, RD No. 18053 (April, 1979), British Pat. No. 1,425,020, and West German Patent Application (OLS) Nos. 2,219,917, 2,261,361, 2,329,587 and 2,433,812. α-Pivaloylacetanilide couplers are excellent in fastness, particularly to light of developed dye. On the other hand, α-benzoylacetanilide couplers provide a high color density.

Examples of magenta couplers which may be used together with the gelatin hardeners of the present invention include oil protect type indazolone or cyanoacetyl couplers. Preferred examples of such couplers include 5-pyrazolone couplers and pyrazoloazole couplers such as pyrazolotriazoles. From the viewpoint of the hue of the colored dye and the color density, the 5-pyrazolone couplers are preferably couplers in which the 3-position in substituted by an arylamino group or acylamino group. Typical examples of such couplers include those described in U.S. Pat. Nos. 2,311,082, 2,343,703, 2,600,788, 2,908,573, 3,062,653, 3,152,896 and 3,936,015. Particularly preferred examples of coupling-off groups of diequivalent 5-pyrazolone couplers include arylthio groups as described in U.S. Pat. No. 4,351,897. 5-Pyrazolone couplers having ballast groups as described in European Pat. No. 73,636 provide a high color density.

As the pyrazoloazole couplers there may be used pyrazolobenzimidazoles as described in U.S. Pat. No. 3,369,879. Preferred examples of pyrazoloazole couplers include pyrazolo[5,1-c][1,2,4]triazoles as described in U.S. Pat. No. 3,725,067, pyrazolotetrazoles as described in *Research Disclosure*, RD No. 24220 (June, 1984), pyrazolopyrazoles as described in *Research Disclosure*, RD No. 24230 (June 1984). Imidazo[1,2-b]pyrazoles described in European Patent 119,741 are advantageous in that the colored dye has less secondary peak of yellow light and shows an excellent fastness to light. Particularly preferred examples of such pyrazoloazole couplers include pyrazolo[1,5-b][1,2,4]triazoles as described in European Pat. No. 119,860.

Examples of cyan couplers which may be used together with the gelatin hardeners of the present invention include oil protect type naphtholic and phenolic couplers. Typical examples of such couplers include naphtholic couplers as described in U.S. Pat. No. 2,474,293. Preferred examples of naphtholic couplers include oxygen atom releasing diequivalent naphtholic couplers as described in U.S. Pat. Nos. 4,052,212, 4,146,396, 4,228,233 and 4,296,200. Specific examples of phenolic couplers include those described in U.S. Pat. Nos. 2,369,929, 2,801,171, 2,772,162 and 2,895,826. In the present invention, cyan couplers fast to heat and moisture may be preferably used. Typical examples of such cyan couplers include phenolic cyan couplers having alkyl groups but methyl groups in the meta-position of its phenol nuclei as described in U.S. Pat. No. 3,772,002, 2,5-diacylamino-substituted phenolic couplers as described in U.S. Pat. Nos. 2,772,162, 3,758,308, 4,126,396, 4,334,011 and 4,327,173, West German Patent Application (OLS) No. 3,329,729, and Japanese Patent Application (OPI) No. 166956/84, and phenolic couplers having phenylureido groups in its 2-position and acylamino groups in its 5-position as described in U.S. Pat. Nos. 3,446,622, 4,333,999, 4,451,559 and 4,427,767.

In order to correct unnecessary absorption of short wavelength by dyes produced from the magenta and cyan couplers, color light-sensitive materials used for photographing preferably comprise colored couplers. Typical examples of such colored couplers include yellow-colored magenta couplers as described in U.S. Pat. No. 4,163,670 and Japanese Patent Publication No. 39413/82 and magenta-colored cyan couplers as described in U.S. Pat. Nos. 4,004,929 and 4,138,258 and British Pat. No. 1,146,368.

Couplers which produce a colored dye having a proper diffusibility may be used together for improving graininess.

The gelatin hardener of the present invention may be used together with those couplers which release a development inhibitor upon development (so-called DIR couplers), As the DIR couplers, there are illustrated those which release a hetercyclic mercapto type development inhibitor; those which release a benzotriazole derivative as a development inhibitor; colorless DIR couplers; those which release a nitrogen-containing heterocyclic development inhibitor involving decomposition of methylol after coupling-off; those which release a development inhibitor involving an intramolecular nucleophilic reaction after coupling-off; those which release a development inhibitor by electron migration via a conjugated system after coupling-of; those which release a diffusible development inhibitor that its development-inhibiting ability will be deactivated in a developer; those which release a reactive compound that produces a development inhibitor, or deactivates a development inhibitor, by a reaction in film upon development; and the like.

Those compounds which release a fogging agent, a development accelerator, or a precursor thereof by a coupling reaction or oxidation-reduction reaction may be used together.

In the case of applying the present invention to the light-sensitive materials, those compounds which release an electron-donative compound or a precursor thereof by the coupling reaction or oxidation-reduction with an oxidation product of a developing agent may be used together.

In the case of using various couplers together with the hardener of the present invention, two or more couplers may be used in one and the same layer of a light-sensitive material, or the same compound may be used in two or more layers for obtaining the properties necessary for the light-sensitive material.

In applying the present invention to silver halide light-sensitive materials, silver halide emulsions to be used are prepared by mixing a solution of a water-soluble silver salt (e.g., silver nitrate) with a solution of a water-soluble halogen salt (e.g., a potassium bromide or a mixture of halogen salts) in the presence of a solution of a water-soluble high polymer such as gelatin. As the thus prepared silver halides, silver chloride, silver bromide, and mixed silver halides such as silver chlorobromide, silver chloroiodobromide, silver iodobromide, etc. are typical. Average grain size of silver halide grains (grain diameter with respect to spherical or approximately spherical grains, or edge length with respect to cubic grains; presented in terms of an average based on projected area) is preferably 0.1 μm to 2 μm. Grain size distribution may be either narrow or broad. So-called mono-disperse silver halide emulsions having a narrow grain size distribution wherein 90% or more, particularly 95% or more, of the all grains by number or by weight fall within ±40% of the average grain size may be used in the present invention.

The silver halide grains to be used in the silver halide emulsion may be in a a regular crystal form such as a cubic, octahedral, dodecahedral or tetradecahedral form, in an irregular form such as a spherical form, or in a mixed form thereof. In addition, tabular grains may also be used. Particularly, emulsions in which silver halide tubular grains of 5 or more, particularly 8 or more, in length-to-thickness ratio account for 50% or more of the total grains based on the projected area of the grains may also be used.

The silver halide emulsion to which the present invention can be applied may be chemically sensitized by conducting sulfur or selenium sensitization, reduction sensitization, noble metal sensitization, etc. alone or in combination.

That is, sulfur sensitization using active gelatin or sulfur-containing compounds capable of reacting with silver (e.g., thiosulfates, thioureas, mercapto compounds, rhodanines, etc.); reduction sensitization using a reductive substance (e.g., stannous salts, amines, hydrazine derivatives, formamidinesulfinic acid, silane compounds, etc.); and noble metal sensitization using metal compounds (e.g., complex salts of metals of Group VIII in the periodic table, such as Pt, Ir, Pd, Rh, Fe, etc. as well as gold complex salts) can be employed alone or in combination.

Photographic emulsion to which the present invention can be applied are spectrally sensitized with photographic sensitizing dyes. Dyes to be used include cyanine dyes, merocyanine dyes, complex cyanine dyes, complex merocyanine dyes, holopolar cyanine dyes, hemicyanine dyes, styryl dyes, and hemioxonol dyes. Particularly useful dyes are those belonging to cyanine dyes, merocyanine dyes, and complex merocyanine dyes. In these dyes, any of nuclei ordinarily used as basic hereto ring nuclei in cyanine dyes can be used.

These sensitizing dyes may be used alone or in combination. Combinations of sensitizing dyes are often employed particularly for the purpose of super-sensitization.

Various compounds may be incorporated in the photographic emulsion to which the present invention can be applied for the purpose of preventing formation of fog or stabilizing photographic properties in the steps of producing light-sensitive materials, or during storage or processing of, light-sensitive materials. That is, many compounds known as antifoggants or stabilizers such as azoles (e.g., benzothiazolium salts, benzimidazolium salts, imidazoles, benzimidazoles (preferably 5-nitrobenzimidazoles) nitroindazoles, benzotriazoles (preferably 5-methylbenzotriazoles), triazoles, etc.); mercapto compounds (e.g., mercaptothiazoles, mercaptobenzothiazoles, mercaptobenzimidazoles, mercaptobenzoxazoles, mercaptoxadiazoles, mercaptothiadiazoles, mercaptotriazoles, mercaptotetrazoles (particularly 1-phenyl-5-mercaptotetrazole, etc.), mercaptopyrimidines, mercaptotriazines, etc.); thiocarbonyl compounds (e.g., oxazolinethione); azaindenes (e.g., triazaindenes, tetrazaindenes (particularly 4-hydroxy-6-methyl-(1,3,3a,7-)tetrazaindene), pentazaindenes, etc.); benzenethiosulfonic acids; benzenesulfinic acids; benzenesulfonic acid amides; purines (e.g., adenine); etc. may be added.

The light-sensitive material prepared according to the present invention may contain one or more surfactants for various purposes such as improvement of coating properties, antistatic properties, sliding properties, emulsion dispersion, anti-adhesion properties, and photographic properties (for example, development acceleration, increasing high contrast, sensitization, etc.).

For example, there can be used nonionic surfactants such as saponins (steriod type), alkylene oxide derivatives (e.g., polyethylene glycol, polyethylene glycol/polypropylene glycol condensates, polyethylene glycol alkyl ethers, polyethylene glycol alkylaryl ethers, polyethylene glycol esters, polyethylene glycol sorbitan esters, polyalkylene glycol alkylamines or amides, silicone polyethylene oxide adducts, etc.), polyhydric alcohol fatty acid esters, sugar alkyl esters, etc.; and anionic surfactants having an acidic group such as a carboxy group, a sulfo group, a phospho group, a sulfuric ester group, or a phosphoric ester group (e.g., alkylcarboxylates, alkylsulfonates, alkylbenzenesulfonates, alkylnaphthalenesulfonates, alkylsulfates, alkylphosphates, N-acyl-N-alkyltaurines, sulfosuccinates, sulfoalkylpolyoxyethylene alkylphenyl ethers, polyoxyethylene alkylphosphates, etc.

As the more preferably used surfactants, there are illustrated fluorine-containing surfactants. As such fluorine-containing surfactants, those compounds which are described in Japanese Patent Publication Nos. 43130/73, 44411/81, and 9303/72 may preferably be used.

In addition to the above-described additives, the light-sensitive material prepared according to the present invention may further contain various stabilizers, stain-preventing agents, developing agents or precursors thereof, development accelerators or precursors thereof, lubricants, mordants, matting agents, antistatic agents, plasticizers, or other various additives useful for photographic light-sensitive materials. Typical examples of these additives are described in *Research Disclosure*, vol. 176, RD No. 17643 (December, 1978) and ibid., vol. 187, RD No. 18716 (November, 1979).

Development processing of the light-sensitive material prepared according to the present invention is not particularly limited, and any of known color development processings and black-and-white development processings may be used. As to development processing, reference may be made to the aforementioned *Research Disclosure*, vol. 176, RD No. 17643 (December 1978).

The gelatin-hardening process of the present invention can be preferably used not only for photographic light-sensitive materials, but also in any industry using hardened gelatin.

For example, the present invention can be applied to the hardening of microcapsules described, for example, in U.S. Pat. No. 4,016,098.

The present invention is now illustrated in greater detail by reference to the following examples which, however, are not to be construed as limiting the present invention in any way.

EXAMPLE 1

Each of compounds 6, 7, 10 and 23 in accordance with the present invention, comparative compound (I) described in U.S. Pat. No. 4,063,952 (Illustrative Compound 15), and comparative compound (II) disclosed in U.S. Pat. No. 3,642,486 (Example II) was added to a 7% gelatin aqueous solution in an amount shown in Table 1, and each of the resulting solutions was uniformly coated on a cellulose triacetate support in a dry thickness of about 8 $\mu$m, then dried to prepare gelatin layers (A) to (K). Also, gelatin layer (L) containing absolutely no hardeners was prepared as a control. These samples were left in an environment of 25° C. and 50% RH (relative humidity), and part of each sample was taken out at intervals of 2 hours, one day, 3 days, and 7 days after coating in order to determine a crosslinking coefficient (crosslinking unit numbers per weight-average molecular weight before crosslinking), $\delta$, according to the following method. Method of determining crosslinking coefficient, $\delta$:

Each gelatin layer was delaminated from the support, and the weight thereof, $M_1$, was measured. A sol component was extracted from each of the gelatin layers with warm water, and the gelatin weight thereof, $M_2$, was determined by a microbiuret method using a biuret reaction. The sol fraction, S, was calculated according to the following formula using the results thus obtained.

$$S = (M_2/M_1)$$

δ was calculated using the thus calculated value, S, according to the following formula described in A. Charlesby, *Atomic Radiation and Polymers*, (published by Pergamon Press, 1960), pp. 134–158.

$$\delta = \frac{2}{S + \sqrt{S}}$$

δ values of gelatin layers (A) to (L) at respective stages are tabulated in Table 1.

TABLE 1

| Gelatin Layer | Hardener | Added Amount (per 100 g of dry gelatin) | δ After 2 hrs. | After 1 day | After 3 days | After 7 days |
|---|---|---|---|---|---|---|
| (A) | Compound 6 of the present invention | 10 mmol | 3.4 | 3.3 | 3.5 | 3.4 |
| (B) | Compound 6 of the present invention | 20 mmol | 5.1 | 5.1 | 5.2 | 5.2 |
| (C) | Compound 7 of the present invention | 10 mmol | 3.5 | 3.6 | 3.4 | 3.6 |
| (D) | Compound 7 of the present invention | 20 mmol | 5.2 | 5.2 | 5.3 | 5.2 |
| (E) | Compound 10 of the present invention | 10 mmol | 3.6 | 3.7 | 3.7 | 3.6 |
| (F) | Compound 10 of the present invention | 20 mmol | 5.3 | 5.2 | 5.4 | 5.3 |
| (G) | Compound 23 of the present invention | 10 mmol | 3.2 | 3.3 | 3.3 | 3.4 |
| (H) | Compound 23 of the present invention | 20 mmol | 5.1 | 5.1 | 5.2 | 5.2 |
| (I) | Comparative compound (I) | 10 mmol | 2.8 | 2.7 | 2.7 | 2.8 |
| (J) | Comparative compound (I) | 20 mmol | 4.5 | 4.3 | 4.4 | 4.4 |
| (K) | Comparative compound (II) | 4 mmol | 1.2 | 2.8 | 4.6 | 5.4 |
| (L) | None (control) | 0 | 1.0 | 1.0 | 1.0 | 1.0 |

Comparative Compound (I)

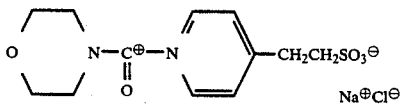

Comparative Compound (II)
$CH_2=CHSO_2CH_2OCH_2SO_2CH=CH_2$

As is seen from the results set forth in Table 1, all of gelatin layers (A) to (H) using Compound 6, 7, 10 or 23 of the present invention underwent such a fast hardening action that the hardening reaction was completed in about 2 hours after the coating and, after that, δ did not change.

Comparative compound (I) showed about the same fast hardening action as Compound 6, 7, 10 or 23, but, in comparison with the systems using Compound 6, 7, 10 or 23 in the equimolar amounts (gelatin layers (A), (C), (E), and (G) with (I), or (B), (D), (F), and (H) with (J)), comparative compound (I) provided a lower δ, which may be probably attributed to its poor selectivity between reactive residues of gelatin and water, thus having less efficiency as a hardener.

On the other hand, comparative compound (II) showed a slow hardening action, and δ increased even after 3 days (post-hardening).

It is apparent, from the above results, that Compounds 6, 7, 10 and 23 of the present invention show a fast hardening action, and are excellent hardeners with excellent efficiency.

EXAMPLE 2

Each of Compound 6 of the present invention and comparative compound (II) was added as shown in Table 2 to a high-speed negative type photographic emulsion prepared in a conventional manner and containing 120 g of gelatin and 65 g of silver iodobromide per kg, and uniformly coated in a dry thickness of 10 μm on a subbed cellulose triacetate support, then dried to prepare samples. After leaving each sample for 7 days at room temperature, the degree of swelling Q, defined by the following formula, was measured in 25° C. water.

$$Q = \frac{\text{Film thickness increased by swelling}}{\text{Dry film thickness}}$$

Separately, a needle with a copper ball of 0.4 mm radius at its end was pressed onto the surface of each sample dipped in water, and was allowed to run in parallel with the surface at a speed of 2.5 mm per second while continuously changing the load to the needle within the range of from 0 to 200 g to determine the load sufficient to damage the film surface.

Further, the thus obtained film samples were wedge exposed, developed at 20° C. for 8 minutes in a developer, D-76, fixed, washed with water, and dried, followed by sensitometry to determine sensitivity and fog. The results thus obtained are tabulated in Table 2.

As is clear from Table 2, the compounds of the present invention provided sufficient film strength to be practically useful without damaging photographic properties.

TABLE 2

| Compound | Amount Added (per 100 g of dry gelatin) | Photographic Properties | | | | Film Strength | |
|---|---|---|---|---|---|---|---|
| | | 7 Days after Coating | | Accelerated conditions (50° C., 2 days) | | Q (7 days) after coating) | Scratch Resistance (g) (7 days after coating) |
| | | Relative Sensitivity | Fog | Relative Sensitivity | Fog | | |
| Control | 0 | 100 | 0.06 | 100 | 0.09 | 9.9 | 7 |
| Compound 6 of the invention | 30 mmol | 98 | 0.06 | 97 | 0.09 | 4.3 | 78 |
| Comparative compound (II) | 5 mmol | 93 | 0.05 | 93 | 0.06 | 4.9 | 74 |

EXAMPLE 3

A silver iodobromide emulsion containing 3.0 mol% silver iodide was prepared, and was subjected to post ripening in the presence of sodium thiosulfate and a gold salt to obtain a high-speed negative emulsion with maximum sensitivity.

This emulsion was mixed with a coupler emulsion prepared by dissolving 1-(2′,4′,6′-trichlorophenyl)-3-[3″-(2″,4″-di-t-amylphenoxyacetamido)benzamido]-5-pyrazolone in a mixture of dibutyl phthalate and tricresyl phosphate and dispersed in a gelatin solution of an o/w type using sorbitan monolaurate, Turkey red oil, and sodium dodecylbenzenesulfonate as dispersing and emulsifying agents. Then, 10.0 g (28 mmol) of Compound 6 of the present invention was added thereto per 100 g of dry gelatin, and the emulsion was coated on a subbed cellulose triacetate support in a dry thickness of about 10 μm and dried to obtain a color film with a single magenta layer.

This experimental color film was wedge exposed, and subjected to color development processing using 4-amino-3-methyl-N-ethyl-β-hydroxyethylaniline sesquisulfate monohydrate as a developing agent, followed by examining color-forming properties by sensitometry.

As a result, it was found that the compound of the present invention did not damage the color-forming properties of the coupler, and formed no color stains.

While the invention has been described in detail and with reference to specific embodiments thereof, it will be apparent to one skilled in the art that various changes and modifications can be made therein without departing from the spirit and scope thereof.

What is claimed is:

1. A process for hardening gelatin, which comprises incorporating in a gelatin-containing material at least one hardening compound represented by formula (I):

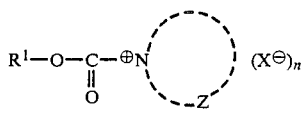

wherein $R^1$ represents a substituted or unsubstituted aryl group, Z represents non-metallic atoms necessary for the formation of a nitrogen-containing heteroaromatic ring which may optionally be substituted, $X^\ominus$ represents an anion, and n represents 0 or 1 provided that when n represents 0, the compound forms an inner salt.

2. A process for hardening gelatin of claim 1, wherein $R^1$ represents a substituted or unsubstituted aryl group having from 6 to 20 carbon atoms.

3. A process for hardening gelatin of claim 1 wherein Z represents non-metallic atoms necessary for the formation of a nitrogen-containing 5- or 6-membered heteroaromatic ring which may optionally be substituted.

4. A process for hardening gelatin of claim 3, wherein Z represents a substituted or unsubstituted pyridine ring or an imidazole ring.

5. A process for hardening gelatin of claim 1, wherein $X^\ominus$ is selected from the group consisting of a halide ion, an alkylsulfonate ion having from 1 to 20 carbon atoms, an arylsulfonate ion having from 6 to 20 carbon atoms, a sulfate ion, a phosphate ion, a phosphonate ion, $BF_4^\ominus$, $ClO_4^\ominus$ and $PF_6^\ominus$.

6. A process for hardening gelatin of claim 5, wherein $X^\ominus$ represents $Cl^\ominus$, $BF_4^\ominus$, $PF_6^\ominus$, an alkylsulfonate ion or an arylsulfonate ion.

7. A process for hardening gelatin of claim 1, wherein the inner salt is formed by bonding between the nitrogen-containing heteroaromatic ring and $X^\ominus$.

8. A process for hardening gelatin of claim 7, wherein $X^\ominus$ is selected from the group consisting of a halide ion, an alkylsulfonate ion having from 1 to 20 carbon atoms, an arylsulfonate ion having from 6 to 20 carbon atoms, a sulfate ion, a phosphate ion, a phosphonate ion, $BF_4^\ominus$, $ClO_4^\ominus$, and $PF_6^\ominus$.

9. A process for hardening gelatin of claim 7, wherein the anion is a sulfo group or a sulfoalkyl group.

10. A process for hardening gelatin of claim 1, wherein the substituents of $R^1$ are selected from the group consisting of a halogen atom,

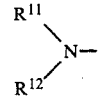

(wherein $R^{11}$ and $R^{12}$ each represents the same substituent as defined for $R^1$ except for a halogen atom and

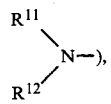

a straight or branched chain alkyl group having from 1 to 20 carbon atoms, an alkoxy group having from 1 to 20 carbon atoms, an aryl group having from 6 to 20 carbon atoms, an aryloxy group having from 6 to 20 carbon atoms, an aralkyl group having from 7 to 20 carbon atoms, and an alkenyl group having from 2 to 20 carbon atoms.

11. A process for hardening gelatin of claim 1, wherein the hardener is used in an amount of from 0.01 to 20wt% based on the weight of dry gelatin.

12. A process for hardening gelatin of claim 11, wherein the hardener is used in an amount of from 0.05 to 10 wt% based on the weight of dry gelatin.

13. A photographic light-sensitive material comprising a support and at least one gelatin-containing layer provided on the support, wherein said gelatin-containing layer contains at least one gelatin hardening compound represented by the formula (I)

wherein $R^1$ represents a substituted or unsubstituted aryl group, Z represents non-metallic atoms necessary for the formation of a nitrogen-containing heteroaromatic ring which may optionally be substituted, $X^\ominus$ represents an anion, and anion, and n represents 0 or 1 provided that when n represents 0, the compound forms an inner salt.

14. A photographic light-sensitive material of claim 13, wherein $R^1$ represents a substituted or unsubstituted aryl group having from 6 to 20 carbon atoms.

15. A photographic light-sensitive material of claim 13, wherein Z represents non-metallic atoms necessary for the formation of a nitrogen-containing 5- or 6-membered heteroaromatic ring which may optionally be substituted.

16. A photographic light-sensitive material of claim 15, wherein Z represents a substituted or unsubstituted pyridine ring or an imidazole ring.

17. A photographic light-sensitive material of claim 13, wherein $X^\ominus$ is selected from the group consisting of a halide ion, an alkylsulfonate ion having from 1 to 20 carbon atoms, an arylsulfonate ion having from 6 to 20 carbon atoms, a sulfate ion, a phosphate ion, a phosphonate ion, $BF_4^\ominus$, $ClO_4^\ominus$ and $PF_6^\ominus$.

18. A photographic light-sensitive material of claim 17, wherein $X^\ominus$ represents $Cl^\ominus$, $BF_4^\ominus$, $PF_6^\ominus$, an alkylsulfonate ion or an arylsulfonate ion.

19. A photographic light-sensitive material of claim 13, wherein the inner salt is formed by bonding between the nitrogen-containing heteroaromatic ring and $X^\ominus$.

20. A photographic light-sensitive material of claim 19, wherein $X^\ominus$ is selected from the group consisting of a halide ion, an alkyl sulfonate ion having from 1 to 20 carbon atoms, an arylsulfonate ion having from 6 to 20 carbon atoms, a sulfate ion, a phosphate ion, a phosphonate ion, $BF_4^\ominus$, $ClO_4^\ominus$, and $PF_6^\ominus$.

21. A photographic light-sensitive material of claim 19, wherein the anion is a sulfo group or a sulfoalkyl group.

22. A photographic light-sensitive material of claim 13, wherein the substituents of $R^1$ are selected from the group consisting of a halogen atom,

(wherein $R^{11}$ and $R^{12}$ each represents the same substituent as defined for $R^1$ except for a halogen atom and

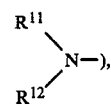

a straight or branched chain alkyl group having from 1 to 20 carbon atoms, an alkoxy group having from 1 to 20 carbon atoms, an aryl group having from 6 to 20 carbon atoms, an aryloxy group having from 6 to 20 carbon atoms, an aralkyl group having from 7 to 20 carbon atoms, and an alkenyl group having from 2 to 20 carbon atoms.

23. A photographic light-sensitive material of claim 13, wherein the hardener is used in an amount of from 0.01 to 20 wt% based on the weight of dry gelatin.

24. A photographic light-sensitive material of claim 23, wherein the hardener is used in an amount of from 0.05 to 10 wt% based on the weight of dry gelatin.

* * * * *